United States Patent
Patel et al.

(10) Patent No.: US 8,574,561 B1
(45) Date of Patent: Nov. 5, 2013

(54) COMPOSITIONS CONTAINING ANTI-DANDRUFF AGENTS

(71) Applicant: L'Oreal, Paris (FR)

(72) Inventors: Kamini Patel, Jersey City, NJ (US); Carmen Castillo-Bucci, Englewood, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/724,576

(22) Filed: Dec. 21, 2012

(51) Int. Cl.
*A61K 8/00* (2006.01)
*A61K 8/02* (2006.01)
*A61K 8/30* (2006.01)

(52) U.S. Cl.
USPC ............ 424/70.1; 424/70.19; 424/70.21; 424/70.22; 424/401

(58) Field of Classification Search
None
See application file for complete search history.

(56) References Cited

U.S. PATENT DOCUMENTS

| | | | |
|---|---|---|---|
| 4,948,576 A | 8/1990 | Verdicchio et al. | |
| 7,871,600 B2 | 1/2011 | Hiraishi et al. | |
| 2003/0202952 A1* | 10/2003 | Wells et al. | 424/70.13 |
| 2007/0104747 A1 | 5/2007 | Masse et al. | |

FOREIGN PATENT DOCUMENTS

| | | |
|---|---|---|
| EP | 117135 | 8/1984 |
| WO | 01/76552 A2 | 10/2001 |
| WO | 03/096998 A1 | 11/2003 |
| WO | 2004/089318 A2 | 10/2004 |
| WO | 2006/110386 A1 | 10/2006 |
| WO | 2012/072424 A2 | 6/2012 |

OTHER PUBLICATIONS

Terry Gerstein, M.S. "Clear Zinc Pyrithione Preparations"—Presented May 24, 1971, Seminar, Washington D.C., J. Soc. Cosmet. Chem., 23, p. 99-114, Feb. 3, 1972.
Internet search results on sulfate-free shampoos, Dec. 4, 2012.
Lubrizol "Clear Anti-Dandruff Shampoo with Octopirox"—Noveon Consumer Specialties, SH-0067(LA), Edition Dec. 9, 2012, reference NM1005-003-09, IL052510-A, p. 140 (IELJ), www.personalcare.noveon.com.

* cited by examiner

*Primary Examiner* — Susan Tran
(74) *Attorney, Agent, or Firm* — L'Oreal USA

(57) ABSTRACT

The present invention is directed towards a composition comprising, in an aqueous medium: (a) at least one anti-dandruff agent; (b) at least one viscosity modifying agent; (c) at least acrylic-based polymeric compound different from the viscosity modifying agent; (d) at least two surfactants chosen from amphoteric surfactants and zwitterionic surfactants; and (e) optionally, at least one conditioning agent. The present invention also relates to a process for the care of hair and/or scalp.

9 Claims, No Drawings

COMPOSITIONS CONTAINING ANTI-DANDRUFF AGENTS

FIELD OF THE INVENTION

The present invention relates to compositions and processes/methods for the cosmetic treatment of the hair and/or of the scalp. In particular, the disclosure relates to cosmetic compositions comprising an anti-dandruff agent, thickening agents and amphoteric and/or zwitterionic surfactants.

BACKGROUND OF THE INVENTION

Numerous anti-dandruff compositions have been proposed in the prior art with a view to combating the formation of dandruff.

For instance, International Patent Application Publication No. WO 2004/089318 describes shampoo compositions having an improved detergent and anti-dandruff action. These compositions contain an anti-dandruff ingredient in combination with detergent surfactants and a polyoxyethylenated derivative of an ester of a fatty acid and of sorbitan.

European Patent Application EP 0 117 135 describes detergent compositions having improved antimicrobial and anti-dandruff properties. These compositions comprise at least one anionic or amphoteric surfactant, at least one nitrogenous polymer, and at least one water-soluble non-particulate substance, such as anti-dandruff agents, sun protection agents, and insecticidal agents.

Finally, International Patent Application Publication No. WO 03/096998 describes shampoo compositions which prevent the formation of dandruff. These compositions contain, as active ingredient, extracts of *Camelia sinensis*, or the active ingredients thereof of the polyphenol type (for example, catechins, flavonoids). These compositions can also comprise additional anti-dandruff agents, and anionic, nonionic, amphoteric, zwitterionic, and/or cationic surfactants.

The compositions of the prior art such as those described above all have the objective of improving the anti-dandruff effect and, optionally, improving detergence. However, there remains today, the challenge of formulating compositions which can effectively solubilize or suspend anti-dandruff agents such as zinc pyrithione while at the same, achieve viscosity, stability and foam quality.

In addition, it is desirable to provide compositions which exhibit better skin tolerance while at the same time conserving good anti-dandruff effectiveness and good properties for use such as ease of distribution and spreadability on the hair and/or scalp, good cleansing, ease of rinsing and providing smoothness and a good feel to the hair.

Moreover, consumers of personal care products and cosmetics consider many factors in selecting products for use. Recently, certain factors have been a focus of and have driven scientific study and product development. These driving factors for hair care products include environmental impact, the extent to which the components condition hair, and the aesthetic quality of the overall product including clarity and foaming/lathering. Further, the effort towards environmental impact awareness is a universal concern and consumers are increasingly selective about the biodegradability of personal care products and cosmetics they purchase.

Hair care products which are sulfate free currently exist on the market, however, they tend to have certain undesirable properties such as lack of lathering or foaming, lack of gentle hair cleansing performance, lack of clarity especially in the presence of oils and fragrances, and poor overall viscosity. It is therefore, desirable to provide a composition which has improved sustainability and is biodegradable and non-toxic as compared to traditional shampoo formulations, while maintaining the favorable viscosity, foaming and cleansing properties.

Thus, it is desirable to provide cosmetic compositions for the cosmetic treatment of the hair and/or the scalp that employ active ingredients such as anti-dandruff agents in combination with other ingredients in order to provide multiple benefits to keratinous substrates such as hair and/or skin. It is also desirable to provide methods of cleansing and conditioning keratinous substrates with such compositions.

SUMMARY OF THE INVENTION

The present disclosure is directed to a composition containing, in an aqueous medium:
 (a) at least one anti-dandruff agent;
 (b) at least one viscosity modifying agent;
 (c) at least one acrylic-based polymeric compound different from the viscosity modifying agent;
 (d) at least two surfactants chosen from amphoteric surfactants and zwitterionic surfactants; and
 (e) optionally, at least one conditioning agent.

Preferably, the above-described composition is free of sulfate-containing anionic surfactants The present invention further relates to a process for the care of keratinous substrates such as hair and/or skin/scalp, involving contacting the keratinous substrates with the above-described composition.

The present invention also relates to a process of stabilizing an anti-dandruff composition using the above-described composition.

It has been surprisingly and unexpectedly discovered that the use of the above-described composition on hair and scalp, results in desirable and beneficial effects on the hair and scalp, such as for example, anti-dandruff efficacy related to preventing and reducing dandruff formation, ease of application and distribution on keratinous substrates, good cleansing, good foaming, rich lather and good conditioning.

It has been surprisingly and unexpectedly discovered that the above-described composition was stable, even in the presence of an anti-dandruff agent, such as zinc pyrithione, which is known in the cosmetic arts to pose stability challenges to formulation in terms of remaining suspended homogeneously and preventing the anti-dandruff agent from settling or separating out from the formulation.

Without wishing to be bound to any one theory, it is believed that the combination of a viscosity modifying agent and an acrylic-based polymeric compound different from the viscosity modifying agent, and present in particular amounts and/or weight ratios to each other in the compositions of the present disclosure, aid in stabilizing the compositions and in providing better suspension to the anti-dandruff agent such as zinc pyrithione.

Excellent foaming, lathering and cleansing qualities may be achieved by the compositions of the present disclosure in the presence of two surfactants chosen from amphoteric surfactants and zwitterionic surfactants without requiring the presence of sulfate-containing anionic surfactants. The absence of or presence of very little amounts of sulfate-containing anionic surfactants in cosmetic compositions have the additional advantage of reducing or minimizing irritation to the scalp or skin and the damage and/or artificial color stripping to the hair that is observed with the use of such surfactants.

The presence of surfactants chosen from anionic surfactants that do not contain sulfate groups, nonionic surfactants and cationic surfactants may provide additional foaming and lathering properties and greater stability. The presence of other ingredients comprising conditioning agents, for example, cationic polymers may provide additional benefits such as greater conditioning, smoothness and excellent feel to the hair.

Thus, one embodiment of the present disclosure is directed to a stable cosmetic composition containing an anti-dandruff agent such as zinc pyrithione, viscosity modifying agents, an acrylic-based polymeric compound different from the viscosity modifying agent, two surfactants chosen from amphoteric surfactants and zwitterionic surfactants, and as optional ingredients, conditioning agents such as cationic polymers, and surfactants chosen from anionic surfactants other than sulfate-containing anionic surfactants, nonionic surfactants and cationic surfactants.

DETAILED DESCRIPTION

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

Other than in the operating examples, or where otherwise indicated, all numbers expressing quantities of ingredients and/or reaction conditions are to be understood as being modified in all instances by the term "about," meaning within 10% to 15% of the indicated number.

"At least one" as used herein means one or more and thus includes individual components as well as mixtures/combinations.

The term "free of sulfate-containing anionic surfactants" means that while it is preferred that no sulfate-containing anionic surfactants be present in the composition, it is possible to have very small amounts of sulfate-containing anionic surfactants in the compositions of the invention provided that these amounts do not materially affect at least one, preferably most, of the advantageous properties of the conditioning compositions of the invention. In particular, "free of sulfate-containing anionic surfactants" means that the compositions of the present disclosure contain less than 0.25% by weight or less than 0.1% by weight, or are free (that is, have 0% by weight) of sulfate-based anionic surfactants.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulfate groups, siloxane groups, and polysiloxane groups. The substituent(s) may be further substituted.

"Alkoxylated" as used herein means —O—CHR—(CH2)n- wherein R represents H or an alkyl group, and wherein n ≥1.

Anti-Dandruff Agents

The at least one anti-dandruff agent may be any active agent which can be used to prevent the appearance of dandruff, to decrease the amount thereof, and/or to cause it to completely disappear. Thus, the at least one anti-dandruff agent may be chosen, for example, from antifungal and/or antibacterial agents.

For example, the at least one anti-dandruff agent may be chosen from:

1) pyridinethione salts, for instance, the calcium, magnesium, barium, strontium, zinc, cadmium, tin, and zirconium salts. In at least one embodiment, the anti-dandruff agent may be the zinc salt of pyridinethione, such as the product sold under the name Zinc Omadine® by the company Arch Personal Care;

2) trihalocarbamides of formula:

wherein Z is chosen from halogen atoms such as chlorine and C1-C4 trihaloalkyl groups such as CF 3;

3) triclosan, represented by the formula:

4) azole compounds such as climbazole, ketoconazole, clotrinazole, econazole, isoconazole, and miconazole;

5) antifungal polymers such as amphotericin B and nystatin;

6) selenium sulfides, for example, those of formula $S_xSe_{8-x}$, wherein x is a number ranging from 1 to 7;

7) 2-pyridone derivatives based on 1-hydroxy-2-pyridone such as 1-hydroxy-4-methyl-2-pyridone, 1-hydroxy-6-methylpyridone, 1-hydroxy-4,6-dimethyl-2-pyridone, 1-hydroxy-4-methyl-6-(2,4,4-trimethylpentyl)-2-pyridone, 1-hydroxy-4-methyl-6-cyclohexyl-2-pyridone, 1-hydroxy-4-methyl-6-(methyl-cyclohexyl)2-pyridone, 1-hydroxy-4-methyl-6-(2-bicyclo[2,2,1]heptyl)-2-pyridone, 1-hydroxy-4-methyl-6 (4-methylphenyl)-2-pyridone, 1-hydroxy-4-methyl-6 [1-[4-nitrophenoxy]-butyl]-2-pyridone, 1-hydroxy-4-methyl-6-(4-cyanophenoxymethyl-2-pyridone), 1-hydroxy-4-methyl-6-(phenylsulfonylmethyl)-2-pyridone, 1-hydroxy-4-methyl-6-(4-bromobenzyl)-2-pyridone and salts thereof; By way of preferred derivative of 1-hydroxy-2-pyridone, mention may be made of the composition sold by Clariant under the trade name Octopirox® (1-hydroxy-4-methyl-6-(2,4,4-trimethyl-penthyl)-2-pyridone, monoethanolamine salt;

8) other anti-dandruff agents, which comprise sulfur in its various forms, cadium sulfide, allantoin; coal tar, wood tar, and derivatives thereof, for instance, oil of cade; salicylic acid; undecylenic acid; fumaric acid; and allylamines such as terbinafine.

According to a preferred embodiment, the at least one anti-dandruff agent may be chosen from zinc pyrithione, salicylic acid, selenium disulfide, and mixtures thereof.

According to another preferred embodiment, the at least one anti-dandruff agent of the present disclosure is chosen from zinc pyrithione, commercially available from Arch Personal Care under the trade name Zinc Omadine®.

The at least one anti-dandruff may be present in the composition disclosed herein in an amount ranging from about 0.001 to about 10% by weight, for example, from about 0.1 to about 5% by weight, or from about 0.2 to about 2% by weight, including all ranges and subranges there-between, relative to the total weight of the composition.

Viscosity Modifying Agents

The viscosity modifying agents of the present disclosure include, but are not limited to, polymers based on acrylic acid crosslinked with an allyl ether of pentaerythritol, or an allyl ether of sucrose, or an allyl ether of propylene. Such polymers are also known as gelling agents and are generally of high molecular weight. Variations of such copolymers are also termed carbomers. The carbomers may have high molecular weights ranging from about 700,000 to about 5,000,000.

Preferred viscosity modifying agents of the present disclosure include carbomers which are commercially available under the tradename Carbopol® from the supplier, Lubrizol, examples of which are Carbopol® 934, 940, 941, 951, 954, 956, 980, 981, 1342, 2984, Carbomer EDT 2001, Carbomer-934P, and Carbomer Ultrez 10. Carbomers may also be commercially available under the tradename TEGO® Carbomer from the supplier, Evonik Industries, examples of which are TEGO® Carbomer 134, 140, 141, and 340 FD.

One particularly preferred viscosity modifying agents of the present disclosure is a carbomer known under the tradename, Carbopol® 980 (company Lubrizol).

The at least one viscosity modifying agent of the present disclosure may further comprise other compounds to improve the viscosity modifying, gellifying and thickening properties of the viscosity modifying agent.

The at least one viscosity modifying agent may be present in the composition disclosed herein in an amount ranging from about 0.01 to about 2% by weight, for example, from about 0.05 to about 1% by weight, or from about 0.1 to about 0.5% by weight, including all ranges and subranges therebetween, relative to the total weight of the composition.

Acrylic-Based Polymeric Compound Different from the Viscosity Modifying Agent

The acrylic-based polymeric compound different from the viscosity modifying agent of the present disclosure may be chosen from a copolymer of two or more monomers consisting of acrylic acid, methacrylic acid or one of their simple esters. Suitable examples of a copolymer of two or more monomers consisting of acrylic acid, methacrylic acid or one of their simple esters, include, but are not limited to, acrylates copolymers.

The acrylic-based polymeric compound different from the viscosity modifying agent of the present disclosure may also be chosen from a copolymer of the ester of methacrylic acid and the polyethylene glycol ether of a C12-C22 fatty alcohol, and one or more monomers of acrylic acid, methacrylic acid, or one of their simple esters.

Suitable examples of a copolymer of the ester of methacrylic acid and the polyethylene glycol ether of a C12-C22 fatty alcohol, and one or more monomers of acrylic acid, methacrylic acid, or one of their simple esters, include, but are not limited to, Acrylates/Beheneth-25 Methacrylate Copolymer and Acrylates/Steareth-20 Methacrylate Copolymer. Other examples are ethyl acrylates/methyl methacrylates copolymer emulsion (chemical name) (INCI name:water (and) acrylates copolymer), which is commercially available from Daito Kasei Kogyo Co., Ltd., under the trade name Daitosol 5000AD. This product is sold in the form of an emulsion that contains water, ethyl acrylates/methyl methacrylates copolymer, sodium dehydroacetate, and laureth-21. Another suitable acrylates copolymer is ethyl methacrylates/N-butyl acrylates/2-methylhexyl acrylates copolymer emulsion (chemical name) (INCI name:water (and) acrylates/ethylhexyl acrylates copolymer), which is also commercially available from Daito Kasei Kogyo Co., Ltd., under the trade name Daitosol 5000SJ. This product is sold in the form of an emulsion that contains water, ethyl methacrylates/N-butyl acrylates/2-methylhexyl acrylates copolymer, and Laureth-20. Other yet other acrylates copolymers include an alkyl (meth)acrylates copolymer emulsion (INCI name: acrylates copolymer), which is commercially available from Nippon LSC Ltd., under the trade name Yodosol GH34F; a styrene/acrylates copolymer emulsion (INCI name), which is commercially available from Nippon LSC Ltd., under the tradename Yodosol GH41F; a styrene/acrylates copolymer emulsion (INCI name), and which is commercially available from BASF under the tradename Joncryl 77 (which contains the copolymer in the form of an ammonia salt, along with water and polypropylene glycol); a Polyacrylates-21 (and) acrylates/dimethylaminoethyl methacrylates copolymer (INCI name), commercially available from Interpolymer under the tradename Syntran® PC5100, the chemical composition of which includes, in addition to water and the two acrylates copolymers having CAS Nos. 68541-61-7 and 67380-24-9 respectively, ethoxylated secondary alcohol (CAS No. 84133-50-6) and sodium laurylpolyethoxyethanol sulfate (CAS No. 68891-38-3); a styrene/acrylates/ammonium methacrylates copolymer (and) butylene glycol (and) sodium Laureth-12 sulfate (INCI name), commercially available from Interpolymer under the tradename Syntran® 5760 as a 40 percent aqueous dispersion; and a polyurethane-10 and PEG-12 dimethicone alcohol copolymer emulsion (INCI name), commercially available from Nippon LSC under the tradename Yodosol PUD (which also includes ethanol, 2-phenoyl-ethanol, and water in the emulsion).

Preferred acrylic-based polymeric compounds different from the viscosity modifying agent for use in the compositions of the present disclosure are acrylates copolymers such as those commercially available from the company Rohm & Haas under the tradename, Aculyn™ 33.

Other preferred acrylic-based polymeric compounds different from the viscosity modifying agent for use in the compositions of the present disclosure are copolymers of the ester of methacrylic acid and the polyethylene glycol ether of a C12-C22 fatty alcohol, and one or more monomers of acrylic acid, methacrylic acid, or one of their simple esters, wherein said copolymers include, but are not limited to, Acrylates/Beheneth-25 Methacrylate Copolymer and Acrylates/Steareth-20 Methacrylate Copolymer. Acrylates/Beheneth-25 Methacrylate Copolymer is commercially available from Dow Chemical, under the tradename, Aculyn™ 28. Acrylates/Steareth-20 Methacrylate Copolymer is commercially available from Dow Chemical, under the tradename, Aculyn™ 22.

Another preferred acrylic-based polymeric compound different from the viscosity modifying agent for use in the compositions of the present disclosure may be partially or totally crosslinked with at least one crosslinking agent. The at least one crosslinking agent can be chosen, for example, from polyunsaturated compounds, such as polyethylenically unsaturated compounds. These compounds can be chosen, for example, from polyalkenyl ethers of sucrose, polyalkenyl ethers of polyols, diallyl phthalates, divinylbenzene, allyl (meth)acrylate, ethylene glycol di(meth)acrylate, methylenebisacrylamide, trimethylolpropane tri(meth)acrylate, diallyl itaconate, diallyl fumarate, diallyl maleate, zinc (meth)acrylate, castor oil derivatives and polyol derivatives manufactured from unsaturated carboxylic acids.

The at least one crosslinking agent that may also be used include, for example, unsaturated monomers comprising at least one reactive group capable of reacting with an unsaturation to form a crosslinked copolymer.

The content of the at least one crosslinking agent generally ranges from 0.01% to 5% by weight, for example, from 0.03% to 3% by weight, and further, for example, from 0.05% to 1% by weight, relative to the total weight of the copolymer.

According to one embodiment, the at least one crosslinked copolymer disclosed herein may, for example, be in the form of a dispersion in water. The number-average size of the copolymer particles in the dispersion generally ranges from 10 nm to 500 nm, for example, from 20 nm to 200 nm, and further, for example, from 50 nm to 150 nm.

These copolymers are described, for example, in Patent Application No. WO 01/76552.

For example, the crosslinked methacrylic acid/ethyl acrylate copolymer in the form of an aqueous dispersion of 30% active material manufactured and sold under the name Carbopol® Aqua SF-1 by the company Lubrizol may be used.

The at least one acrylic-based polymeric compound different from the viscosity modifying agent for use in the compositions of the present disclosure may be present in the composition disclosed herein in an amount ranging from about 0.0.05 to about 5% by weight, for example, from about 0.25 to about 3% by weight, or from about 0.1 to about 1% by weight, including all ranges and subranges there-between, relative to the total weight of the composition.

In preferred embodiments of the present disclosure, the weight ratio of the at least one viscosity modifying agent to the at least one acrylic-based polymeric compound different from the viscosity modifying agent in the composition of the present disclosure is at about 1:1, all weights being based on the total weight of the composition.

Amphoteric Surfactants and Zwitterionic Surfactants

The at least two surfactants chosen from amphoteric surfactants and zwitterionic surfactants for use in the present disclosure include alkyl, alkyl dimethyl, alkylamido, alkyl amide, alkylamidopropyl, or alkyl dimethylammonium betaine; alkyl amidopropyl or alkyl sulfobetaine; alkyl, alkylampho, or alkylamphocarboxy glycinate; alkyl, or alkyl substituted imidazoline mono or dicarboxylate; sodium salts of alkyl mono-or dicarboxylates; alkyl beta amino acids; alkyl amidopropyl, or alkyl ether hydroxysultaine; alkyl amidopropyl dimethyl ammonia acetate; alkyl ampho mono-or diacetate; alkyl, or alkyl ampho, or alkyl imino dipropionate; alkyl amphopropionate; alkyl beta amino propionic acid; alkyl dipropionate; alkyl beta iminodipropionate; branched or n-alkyl dimethylamidopropionate; alkyl carboxylated propionate; alkyl, or methyl alkyl imidazoline; fluorinated alkyl amphoteric mixtures; and/or nonionic surfactants such as, but not limited to, alkyl, alkyl dimethyl, alkyl amidopropylamine, or bis 2-hydroxy ethyl alkyl amine oxides; alkanolamides; alkyl amides; polyoxyethylene glycol (PEG) of monoglycerides, of sorbitan esters, of branched or linear fatty alcohol ethers, of branched or linear fatty acid ethers, of thioethers; alkyl oxoalcohol PEG; PEG fatty esters; polyoxyethlyene glycol/polyoxpropylene glycol block copolymers; alkyl phenol PEG ethers; alkyl polyglucosides, or polysaccarides, polysiloxane polyethoxylene ether and mixtures thereof. Specific examples include cocamidopropyl betaine, lauramidopropyl betaine, coco/oleamidopropyl betaine, coco betaine, oleyl betaine, cocamidopropyl hydroxysultaine, tallowamidopropyl hydroxysultaine and dihydroxyethyl tallow glycinate and mixtures thereof.

The amphoteric and zwitterionic surfactants for use in the present disclosure are preferably chosen from (C8-20)alkylbetaines, sulphobetaines, (C8-20 alkyl)amido(C6-8 alkyl)betaines, and (C8-20 alkyl)-amido (C6-8 alkyl)sulphobetaines, (C8-20)alkyl amphocarboxyglycinate and (C8-20)alkyl amphocarboxypropionate, and mixtures thereof.

Preferred amphoteric and zwitterionic surfactants for use in the present disclosure are chosen from (C8-20)alkylbetaines and (C8-20 alkyl)amido(C6-8 alkyl)betaines, for example, cocamidopropyl betaine and coco-betaine. Cocamidopropyl betaine is commercially available from Evonik Industries, under the tradename, TEGO® Betain F 50. Cocobetaine is commercially available from Evonik Industries, under the tradename, TEGO® Betain AB 1214.

The at least two surfactants chosen from amphoteric surfactants and zwitterionic surfactants of the present disclosure may be present in an amount from about 0.1 by weight to about 30% by weight, typically in an amount from about 0.5 by weight to about 20% by weight and more typically from about 1 by weight to about 10% by weight, including all ranges and subranges there-between, based on the total weight of the composition.

In preferred embodiments of the present disclosure, the weight ratio of (C8-20 alkyl)amido(C6-8 alkyl)betaines to (C8-20)alkylbetaines in the composition of the present disclosure, is at about 2:1, all weights being based on the total weight of the composition.

In a particularly preferred embodiment of the present disclosure, the at least two surfactants chosen from amphoteric surfactants and zwitterionic surfactants comprise cocamidopropyl betaine and coco-betaine, present in weight ratio of about 2:1, all weights being based on the total weight of the composition.

Without being bound to any one theory, it is believed that the presence of two different types of amphoteric surfactants such as cocamidopropyl betaine and coco-betaine and their weight proportion to one another may impact the viscosity or rheology as well as the stability of the compositions of the present invention.

A very viscous or thick composition can adversely affect the ease of distribution of the composition on the hair.

A very thin or "runny" composition can impact the application of the composition on the hair as well as the stability of the composition such that settling of the anti-dandruff agent may occur.

Conditioning Agents

The at least one conditioning agent that may be present in the compositions of the present disclosure include, but are not limited to, conditioning polymers chosen from cationic polymers and ampholytic polymers, natural oils, synthetic oils, fatty esters, and mixtures thereof. Non-limiting examples of conditioning agents include quaternium-27, behenamidopropyl PG-dimonium chloride, hydroxyethyl tallowedimonium chloride, stearalkonium chloride and cetrimonium chloride. Other conditioners may include those that are naturally derived.

Non-limiting examples of cationic polymers and ampholytic polymers include hexadimethrine chloride, polyquaternium-4, polyquaternium-6, polyquaternium-7, polyquaternium-10, polyquaternium-11, polyquaternium-16, polyquaternium-22, polyquaternium-32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and polyquaternium-39.

Preferred conditioning agents in the compositions of the present disclosure are chosen from polyquaternium-7, commercially available from Lubrizol, under the tradename, Merquat™ 550PR, polyquaternium-10, commercially available from Dow Chemical, under the tradename, Ucare™ Polymer JR 400, polyquaternium-39, commercially available from Nalco (Lubrizol), under the tradename, Merquat™ 3330 PR Polymer, and polyquaternium-53, commercially available from Nalco (Lubrizol), under the tradename, Merquat™ 2003 PR Polymer.

The at least one conditioning agent of the present disclosure may be present in the composition disclosed herein in an amount of at least about 0.02% by weight, or ranging from about 0.025 to about 3% by weight, or from about 0.025 to about 1% by weight, including all ranges and subranges there-between, relative to the total weight of the composition.

Aqueous Medium

The aqueous medium of the present disclosure may comprise water and mixtures of water and at least one cosmetically acceptable solvent chosen from organic solvents. Suitable organic solvents are typically C1-C4 lower alcohols and polyols alcohols. Examples of organic solvents include, but are not limited to, ethanol, isopropyl alcohol, benzyl alcohol and phenyl ethyl alcohol; glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, isododecane, polybutene, hydrogenated polyisobutene, hydrogenated polydecene, polydecene, squalene, petrolatum and isoparaffins; and mixtures, thereof.

The aqueous medium can be present in the compositions of the present disclosure in the amount of about 95%, 90%, 80%, 70%, 60%, 50%, 40%, 30%, 20%, 10%, 5% by weight or less, based on the total weight of the composition. Additionally, aqueous medium can be present in the compositions of the present disclosure in the amount of from about 20% to about 95% by weight, or from about 50% to about 90% by weight, or from about 60% to about 80% by weight, based on the total weight of the compositions.

Additional Surfactants

The compositions can further comprise at least one surfactant selected from nonionic surfactants, anionic surfactants, amphoteric surfactants and zwitterionic surfactants different from the amphoteric and zwitterionic surfactants which are present in the compositions of the present disclosure and mixtures thereof.

Non-limiting examples of nonionic surfactants includes alkoxylated derivatives of the following: fatty alcohols, alkyl phenols, fatty acids, fatty acid esters and fatty acid amides, wherein the alkyl chain is in the C12-50 range, typically in the C16-40 range, more typically in the C24 to C40 range, and having from about 1 to about 110 alkoxy groups. The alkoxy groups are selected from the group consisting of C2-C6 oxides and their mixtures, with ethylene oxide, propylene oxide, and their mixtures being the typical alkoxides. The alkyl chain may be linear, branched, saturated, or unsaturated. Of these alkoxylated non-ionic surfactants, the alkoxylated alcohols are typical, and the ethoxylated alcohols and propoxylated alcohols are more typical. The alkoxylated alcohols may be used alone or in mixtures with those alkoxylated materials disclosed herein-above.

Commercially available nonionic surfactants are Brij® nonionic surfactants from Croda, Inc. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij® 72 (i.e., Steareth-2) and Brij® 76 (i.e., Steareth-10).

Also useful herein as nonionic surfactants are alkyl glycosides, which are the condensation products of long chain alcohols, which are the condensation products of long chain alcohols, e.g. C8-C30 alcohols, with sugar or starch polymers. These compounds can be represented by the formula (S)n —O—R wherein S is a sugar moiety such as glucose, fructose, mannose, galactose, and the like; n is an integer of from about 1 to about 1000, and R is a C8-C30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a C8-C20 alkyl group, and n is an integer of from about 1 to about 9. Commercially available examples of these surfactants include decyl glucoside (available as Plantacare® 2000 UP) and lauryl glucoside (available as Plantaren® 1200 N UP and Plantacare® 1200 UP), all the above-identified polyglucosides are available from BASF. Also useful herein sucrose ester surfactants such as sucrose cocoate and sucrose laurate.

Other nonionic surfactants suitable for use in the present invention are glyceryl esters and polyglyceryl esters, including but not limited to, glyceryl monoesters, typically glyceryl monoesters of C16-C22 saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of C16-C22 saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of C16-C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan oleate (e.g., Span® 80 from Croda, Inc.), sorbitan sesquioleate (e.g., Span® 83), sorbitan isostearate (e.g., Span® 120), sorbitan stearate (e.g., Span® 60), sorbitan trioleate (e.g., Span® 85), sorbitan tristearate (e.g., Span® 65), and sorbitan palmitate (e.g., Span® 40). All the above-identified sorbitan esters are available from Croda, Inc.

Non-limiting examples of anionic surfactants include compounds in the classes known as alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, isethionates and mixtures thereof. Specific examples of anionic surfactants include the ammonium, monoethanolamine, diethanolamine, triethanolamine, isopropylamine, sodium, potassium, lithium, or magnesium salts of dodecylbenzene-sulfonate, lauryl sulfosuccinate, lauryl ether carboxylate, lauryl sarcosinate, cocomethyl tauride, and sulfosuccinate half ester amide and mixtures thereof.

In preferred embodiments of the compositions of the present disclosure, the compositions are free of sulfate-containing anionic surfactants.

The amphoteric and zwitterionic surfactants which may additionally be employed are different from the amphoteric and zwitterionic surfactants which are present in the compositions of the present disclosure.

Non-limiting examples of amphoteric and zwitterionic surfactants include the earlier described amphoteric and zwitterionic surfactants.

The at least one surfactant chosen from nonionic surfactants, anionic surfactants, amphoteric surfactants and zwitterionic surfactants different from the amphoteric and zwitterionic surfactants which are present in the compositions of the present disclosure is typically present in an amount from about 0.1 to about 45% by weight, typically in an amount from about 5 to about 30% by weight or typically from about 10 to 20% by weight, including all ranges and subranges there-between, based on the total weight of the composition.

In preferred embodiments, the compositions of the present disclosure are free of sulfate-containing anionic surfactants, also defined herein as sulfate-containing anionic detersive surfactants. Examples of sulfate-containing surfactants are the alkyl and alkyl ether sulfates. These materials have the respective formulae: $ROSO_3M$ and $RO(C_2H_4O)_xSO_3M$ wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Other examples of sulfate-containing anionic surfactants are the water-soluble salts of organic, sulfuric acid reaction products conforming to the formula $[R^1SO_3M]$ where $R^1$ is a straight or branched chain, saturated, aliphatic hydrocarbon radical having from about 8 to about 24, preferably about 10 to about 18, carbon atoms; and M is a cation described hereinbefore.

Auxiliary Ingredients

The composition may optionally contain at least one auxiliary ingredient. The auxiliary ingredients may include in particular, film forming agents, proteins, amino acids, skin and hair active agents, sunscreens, viscosity modifiers different from the viscosity modifying agents described hereinbefore, antibacterial agents, preservatives, pH adjusting agents, perfumes, sequestering agents, and mixtures thereof.

Non-limiting examples of film forming agents can be chosen from anionic compounds, non-ionic compounds, amphoteric compounds, zwitterionic compounds, proteins, viscosity modifiers different from the viscosity modifying agents described hereinbefore, cationic polymers different from the cationic polymers described hereinbefore, polyamides, polyaminoamides, polyesters, silicone resins, polysaccharides, silicone fluids, polyacrylamides, starches, gums and mixtures thereof.

Non-limiting examples of viscosity modifiers different from the viscosity modifying agents described hereinbefore include water swellable/soluble cationic polymers from quaternized polysaccharides such as trimethyl ammonium substituted epoxide of hydroxyethyl cellulose, diallyldimethyl ammonium salts of hydroxyethylcellulose, deacylated chitin or chitosan, dihydroxypropyl chitosan trimonium chloride, hydroxypropltrimethyl ammonium chloride guar, locust bean, or konjac mannan gum; quaternized synthetics such as acrylamide dimethyl diallyl ammonium chloride copolymers, acrylamide/dimethyl diallyl ammonium chloride/acrylic acid terpolymer, quaternized poly (vinyl pyrrolidone/dimethyl amino ethylmethacrylate), poly (vinylpyrrolidone/methacrylamidopropyl trimethylammonium chloride), polyvinyl pyrrolidone/methylvinylimidazolinium chloride or methyl sulfate copolymer, chloroethylether/dimethylaminopropylamine/adipate or azelate terpolymer, vinylpyrrolidone/methacrylamidopropyl trimethylammonium chloride, acrylonitrile/acrylic acid/dimethylpropanediammonium acrylates sulfate terpolymer.

Further suitable viscosity modifiers include anionic or nonionic polysaccharide polymers such as gum tragacanth, sodium or propylene glycol alginate, kappa-, iota-, or lambda-carrageenan, guar or hydroxylpropyl guar gum, karaya gum, gum arabic, locust bean gum, konjac mannan gum, gellan, xanthan, succinoglycan or its acidic or enzymatic hydrolysates, sodium carboxymethyl cellulose, methycellulose, hydroxyethylcellulose, hydroxypropylmethylcellulose, and hydroxypropylcellulose; and/or hydrophobically modified anionic, cationic, or nonionic polymers such as, but not limited to, alkyl and/or substituted hydroxyethylcellulose, lauryl dimethyl ammonium substituted epoxide of hydroxyethylcellulose, propoxylated cellulosic, xanthan, succinoglycan, or polygalactomannoses, alkyl methacrylates/crosslinked acrylic acid copolymer and/or acrylonitrile/acrylates block copolymer.

Non-limiting examples of antibacterial agents include bacitracin, phenol, benzethonium chloride, erythromycin, neomycin, tetracycline, chlortetracycline and mixtures thereof.

Non-limiting examples of preservatives include polyvinyl alcohol, phenoxyethanol, benzyl alcohol, methyl paraben, propyl paraben and mixtures thereof.

Non-limiting examples of pH adjusting agents include potassium acetate, sodium carbonate, sodium hydroxide, phosphoric acid, succinic acid, sodium citrate, citric acid, boric acid, lactic acid, sodium hydrogen carbonate and mixtures thereof.

The at least one auxiliary ingredient is present in the composition in a preferred amount of from 0.001 to 50% and more preferably from 0.01 to 20% by weight, based on the total weight of the composition.

In particularly preferred embodiments of the present disclosure, the compositions are substantially free, that is, less than 0.25% by weight, of silicones, based on the total weight of the composition.

In preferred embodiments of the present disclosure, a pH reading of the compositions of the present disclosure ranges from about 3.5 to about 6.5, such as from about 4.0 to about 4.6.

The cosmetic compositions of the present disclosure can be in the form of an aqueous composition or an emulsion, such as a lotion or cream. Such compositions can be useful as compositions for cleansing and conditioning keratinous substrates such as hair or skin or scalp.

The compositions of the present disclosure include hair care products such as shampoos and conditioners, products for cleansing and conditioning the hair and the skin/scalp, and products for cosmetically treating or for the care of the hair or skin/scalp.

Preferred embodiments of the compositions of the present disclosure include anti-dandruff shampoos/conditioners/treatments, and scalp treatment compositions.

Other preferred embodiments of the compositions of the present disclosure include compositions that can be applied onto hair and/or skin/scalp before or after shampooing or cleansing the hair and/or skin/calp.

The method of treatment to be provided will depend on the keratinous substrate being targeted and, consequently, on the specific ingredients contained in the composition used to effectuate the treatment. One of ordinary skill in the art will easily be able to determine these variables.

One embodiment of the present disclosure is a composition containing an anti-dandruff agent such as zinc pyrithione, viscosity modifying agents, acrylic-based polymeric compounds different from the viscosity modifying agent as described hereinbefore, surfactants chosen from amphoteric surfactants and zwitterionic surfactants, wherein the composition is free of sulfate-containing anionic surfactants.

Another embodiment of the present disclosure is a composition containing an anti-dandruff agent such as zinc pyrithione, viscosity modifying agents, acrylic-based polymeric compounds different from the viscosity modifying agent, surfactants chosen from amphoteric surfactants and zwitterionic surfactants, conditioning agents such as cationic polymers, additional surfactants chosen from anionic surfactants that do not contain sulfate groups, nonionic surfactants and cationic surfactants. Preferably, said composition is free of sulfate-containing anionic surfactants.

A preferred embodiment of the present disclosure is a cleansing or cleansing/conditioning composition containing an anti-dandruff agent such as zinc pyrithione, viscosity modifying agents, acrylic-based polymeric compounds different from the viscosity modifying agent as described hereinbefore, surfactants chosen from amphoteric surfactants and zwitterionic surfactants, wherein the composition is free of sulfate-containing anionic surfactants.

A particularly preferred embodiment of the present disclosure is an anti-dandruff composition containing zinc pyrithione, viscosity modifying agents, acrylic-based polymeric compounds different from the viscosity modifying agent as described hereinbefore, surfactants chosen from amphoteric surfactants and zwitterionic surfactants, wherein the composition is free of sulfate-containing anionic surfactants.

Other embodiments of the present disclosure relate to a process for cosmetically treating or caring for the hair and/or scalp involving contacting the hair and/or scalp with the above-described compositions. In particular, said process is employed in order to reduce or prevent dandruff formation on the hair and/or scalp.

One embodiment of the present disclosure relates to a process for cleansing the hair and/or scalp involving contacting the hair and/or scalp with the above-described compositions. At the same time, said cleansing process is employed in order to reduce or prevent dandruff formation on the hair and/or scalp.

Also disclosed herein is a process for cosmetically treating hair and/or scalp involving contacting the hair and/or scalp with an effective amount of the above-described compositions.

According to at least one embodiment, such a process comprises contacting the hair with an effective amount of the composition of the present disclosure, and optionally rinsing it out after it has optionally been left on the hair for a period of time.

When the composition according to the present disclosure is applied in the form of a lotion or a cream before or after shampooing, it is optionally left on the hair for a time period ranging from 30 seconds to 5 minutes, and then optionally rinsed out with water.

The compositions of the present disclosure may be used in direct application to keratinous substrates such as hair and/or skin/scalp, or in a conventional manner for cleansing hair and skin/scalp and controlling microbial infection or dandruff formation on the hair or skin/scalp. The present invention may be used for treating or cleansing of the skin or hair of animals as well.

An effective amount of the composition, typically from about 1 gram to about 50 grams, preferably from about 1 gram to about 20 grams of the composition, for cleansing hair, scalp, skin or other area of the body, is topically applied to the hair, scalp skin or other area that has preferably been wetted, generally with water. The composition is then rinsed off. Application to the hair typically includes working the composition, for example, a shampoo composition through the hair.

A preferred method for providing anti-dandruff efficacy with a shampoo embodiment comprises the steps of: (a) wetting the hair with water, (b) applying an effective amount of the anti-dandruff shampoo composition to the hair, and (c) rinsing the anti-dandruff shampoo composition from the hair using water. These steps may be repeated as many times as desired to achieve the cleansing, conditioning, and anti-dandruff benefits sought.

A further embodiment of the present invention comprises a method comprising the steps of (a) wetting the hair with water, (b) applying an effective amount of a shampoo composition comprising zinc pyrithione or a polyvalent metal salt of pyrithione, (c) rinsing the shampoo compositions from the hair using water; (d) applying a conditioner composition; and (e) rinsing the conditioner composition from the hair using water.

One other embodiment of the present invention comprises a method of stabilizing a composition containing an anti-dandruff such as zinc pyrithione, by employing a combination a viscosity modifying agent chosen from carbomers and an acrylic-based polymeric compound different from the viscosity modifying agent in a weight ratio of about 1:1, and two surfactants comprising in a weight ratio of about 2:1.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1

Formulation examples of the inventive composition

|  | Formula A | Formula B | Formula C |
|---|---|---|---|
| ACRYLATES COPOLYMER (Aculyn ™ 33) | 0.420 | 0.420 | 0.420 |
| CARBOMER (Carbopol ® 980) | 0.392 | 0.343 | 0.343 |
| COCAMIDOPROPYL BETAINE | 3.800 | 4.560 | 4.560 |
| COCO-BETAINE | 1.740 | 1.800 | 1.800 |
| ZINC PYRITHIONE | 0.990 | 0.990 | 0.990 |
| POLYQUATERNIUM-10 | 0.273 | — | — |
| POLYQUATERNIUM-7 | 0.027 | — | — |
| POLYQUATERNIUM-39 | — | — | 0.185 |
| POLYQUATERNIUM-53 | — | 0.185 | — |
| DECYL GLUCOSIDE | 1.590 | 1.590 | 1.590 |
| PPG-5-CETETH-20 | 0.500 | 0.500 | 0.500 |
| PEG-55 PROPYLENE GLYCOL OLEATE | 0.280 | 0.280 | 0.280 |
| DISODIUM LAURETH SULFOSUCCINATE | 3.125 | 3.125 | 3.125 |

-continued

| | Formula A | Formula B | Formula C |
|---|---|---|---|
| SODIUM LAUROYL SARCOSINATE | 1.500 | 1.500 | 1.500 |
| SODIUM LAURYL SULFOACETATE | 3.125 | 3.125 | 3.125 |
| GLYCOL DISTEARATE | 1.350 | 1.350 | 1.350 |
| PROPYLENE GLYCOL | 0.280 | 0.280 | 0.280 |
| ISOPROPYL ALCOHOL | 0.001 | — | — |
| SALICYLIC ACID | 0.200 | 0.200 | 0.200 |
| SODIUM ACETATE | 0.005 | — | — |
| SODIUM BENZOATE | 0.416 | 0.415 | 0.423 |
| SODIUM CHLORIDE | 1.082 | 1.230 | 1.230 |
| PHENOXYETHANOL | — | 0.006 | — |
| SODIUM POLYNAPHTHALENESULFONATE | 0.041 | 0.041 | 0.041 |
| METHYLISOTHIAZOLINONE | 0.000 | 0.000 | 0.000 |
| BENZOIC ACID | 0.075 | 0.075 | 0.075 |
| CELLULOSE GUM | 0.006 | 0.006 | 0.006 |
| FRAGRANCE | 0.600 | 0.600 | 0.600 |
| WATER | QS 100 | QS 100 | QS 100 |

Procedure for making Formula A:
Main Kettle:
1. Water and polyquaternium-10 are mixed.
2. A portion of sodium lauryl sulfoacetate and disodium laureth sulfosuccinate are added and mixing is continued.
3. Carbomer is added and mixed until completely dispersed.
4. The remainder of sodium lauryl sulfoacetate and disodium laureth sulfosuccinate are added and mixed carefully to avoid aeration. The mixture is then heated to between 80-85° C.
5. Acrlates copolymer is added and mixed until uniform.
6. At 80-85° C., glycol distearate is added and mixed until completely melted.
7. Water is added to start cooling the batch.
8. Sodium lauroyl sarcosinate is added and mixed until completely dispersed.
9. At 40 C, decyl glucoside is added and mixed until uniform. Coiling to 25 C is continued.
10. Zinc pyrithione is added and the mixture is homogenized until uniform.
11. Polyquaternium-7 is added and mixed until uniform.
12. Preservatives and fragrance are added and mixed well between each addition.
13. Coco-betaine and cocamidopropyl betaine are added. The mixture is mixed well.
14. pH and viscosity are checked.

Stability Testing

The stability of the inventive formulations were tested at room temperature, 4° C., 37° C., 45° C. over a period of 8 weeks (week 1, 2, 4 and 8). The formulations were found to be stable, that is, no visible layers or phases and/or no settling of the Zn pyrithione to the bottom of the formulations and/or no grainy texture to the formulas were observed. This indicated that the Zn pyrithione remained homogeneously suspended in the formulations. The stability results at 45° C. also indicate that the formulations are stable up to one year at room temperature.

Performance Testing—Salon Study

The inventive formulations were employed as hair cleansing compositions and were tested on the hair and/or scalp of human models in a salon.

Method of Application:

A measured amount of each formulation was applied onto the hair of the designated models and the formulation was spread and worked through the hair and scalp of the designated models by a licensed professional. The formulations were then rinsed off the hair by warm water.

The inventive formulations demonstrated the following cosmetic attributes: satisfactory viscosity, ease of distribution of the formula on hair, satisfactory foaming, satisfactory cleansing, rich lather, and provides smooth texture to the hair.

Example 2

Comparative Formulation Examples

| | D* | E** | F*** | G**** | H***** | I****** |
|---|---|---|---|---|---|---|
| ACRYLATES COPOLYMER (Aculyn™ 33) | — | 0.420 | 0.420 | — | 0.420 | 0.420 |
| ACRYLATES COPOLYMER (Carbopol® Aqua SF-1) | | | | 0.420 | | |
| CARBOMER (Carbopol® 980) | — | — | — | 0.392 | 0.392 | — |
| COCAMIDOPROPYL BETAINE | — | — | 6.004 | 6.004 | — | 3.800 |
| COCO-BETAINE | 4.740 | 4.740 | — | — | 4.740 | 1.740 |
| ZINC PYRITHIONE | 0.990 | 0.990 | 0.990 | 0.990 | 0.990 | 0.990 |
| POLYQUATERNIUM-10 | 0.637 | 0.637 | 0.637 | 0.637 | 0.637 | 0.637 |
| GUAR HYDROXYPROPYLTRIMONIUM CHLORIDE | — | — | 0.491 | — | — | 0.491 |
| DECYL GLUCOSIDE | 1.590 | 1.590 | 1.590 | 1.590 | 1.590 | 1.590 |
| PPG-5-CETETH-20 | 0.500 | 0.500 | 0.500 | 0.500 | 0.500 | 0.500 |
| PEG-55 PROPYLENE GLYCOL OLEATE | 0.280 | 0.280 | 0.280 | 0.280 | 0.280 | 0.280 |
| PEG-150 PENTAERYTHRITYL TETRASTEARATE | 0.315 | 0.315 | — | — | — | — |
| PPG-2 HYDROXYETHYL COCAMIDE | 0.210 | 0.210 | — | — | — | — |
| DISODIUM LAURETH SULFOSUCCINATE | 3.125 | 3.125 | 3.125 | 3.125 | 3.125 | 3.125 |
| SODIUM LAUROYL SARCOSINATE | 1.500 | 1.500 | 1.500 | 1.500 | 1.500 | 1.500 |
| SODIUM LAURYL SULFOACETATE | 3.125 | 3.125 | 3.125 | 3.125 | 3.125 | 3.125 |
| GLYCOL DISTEARATE | 1.350 | 1.350 | 1.350 | 1.350 | 1.350 | 1.350 |
| DIMETHICONE | — | — | — | — | — | — |

-continued

| | D* | E** | F*** | G**** | H***** | I****** |
|---|---|---|---|---|---|---|
| DIMETHICONOL | — | — | — | — | — | — |
| PROPYLENE GLYCOL | 0.280 | 0.280 | 0.280 | 0.280 | 0.280 | 0.280 |
| SALICYLIC ACID | 0.200 | 0.200 | 0.200 | 0.200 | 0.200 | 0.200 |
| SODIUM BENZOATE | 0.415 | 0.415 | 0.415 | 0.415 | 0.415 | 0.415 |
| SODIUM CHLORIDE | 1.038 | 1.038 | 1.117 | 1.038 | 1.038 | 1.088 |
| ISOPROPYL ALCOHOL | 0.003 | 0.003 | 0.003 | 0.003 | 0.003 | 0.003 |
| FUMARIC ACID | — | — | 0.009 | — | — | 0.009 |
| SODIUM ACETATE | 0.011 | 0.011 | 0.011 | 0.011 | 0.011 | 0.011 |
| BENZOIC ACID | 0.075 | 0.075 | 0.075 | 0.075 | 0.075 | 0.075 |
| METHYLISOTHIAZOLINONE | 0.000 | 0.000 | 0.000 | 0 | 0 | 0.000 |
| CELLULOSE GUM | 0.006 | 0.006 | 0.006 | 0.006 | 0.006 | 0.006 |
| SODIUM POLYNAPHTHALENE-SULFONATE | 0.041 | 0.041 | 0.041 | 0.041 | 0.041 | 0.041 |
| FRAGRANCE | 0.800 | 0.800 | 0.800 | 0.800 | 0.800 | 0.800 |
| WATER | QS 100 | QS 100 | QS 100 | QS 100 | QS 100 | QS 100 |
| Stability Test | Not stable | Not stable | Not stable | Stable | stable | Stable |
| Performance | Not tested for performance | Not tested for performance | Not tested for performance | distribution on the hair was not easy | unsatisfactory conditioning effect | satisfactory |
| Viscosity or rheology | | | | Very thick | | Unsatisfactory at 45° C. |

*Formula D No acrylate copolyme, no carbomer, No cocamidopropyl betaine
**Formula E No carbomer, No cocamidopropyl betaine
***Formula F No carbomer, no coco-betaine
****Formula G No coco-betaine
*****Formula H No cocamidopropyl betaine
******Formula I No carbomer Salon testing, viscosity/rheology and stability testing (according to description in Example 1):

Formulas G, H, and I were stable but they did not perform well on the hair in a salon test and/or did not have satisfactory thickness or rheology.

The foregoing description illustrates and describes the present disclosure. Additionally, the disclosure shows and describes only the preferred embodiments of the disclosure, but, as mentioned above, it is to be understood that it is capable of changes or modifications within the scope of the concept as expressed herein, commensurate with the above teachings and/or skill or knowledge of the relevant art. The embodiments described hereinabove are further intended to explain best modes known of practicing the invention and to enable others skilled in the art to utilize the disclosure in such, or other, embodiments and with the various modification required by the particular applications or uses disclosed herein. Accordingly, the description is not intended to limit the invention to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed is:

1. An anti-dandruff composition comprising, in an aqueous medium:
    (a) from about 0.2 to about 2% by weight of at least one anti-dandruff agent comprising zinc pyrithione;
    (b) from about 0.1 to about 0.5% by weight of at least one viscosity modifying agent chosen from carbomer;
    (c) from about 0.1 to about 1% by weight of at least one acrylic-based polymeric compound different from (b) chosen from acrylates copolymer, acrylates/beheneth-25 methacrylate copolymer, acrylates/steareth-20 methacrylate copolymer and mixtures thereof;
    (d) from about 1 to about 10% by weight of two surfactants comprising: (i) (C8-20 alkyl) amido(C6-8 alkyl) betaines and (ii) (C8-20) alkylbetaines wherein the weight ratio of (i) to (ii) in the composition is at about 2:1;
    (e) from about 0.025 to about 1% by weight of at least one conditioning agent chosen from cationic polymers and ampholytic polymers; and
    (f) at least one surfactant chosen from anionic surfactants other than sulfate-containing anionic surfactants, non-ionic surfactants, amphoteric or zwitterionic surfactants different from the two surfactants in (d), and cationic surfactants;
    all weights being relative to the total weight of the composition;
    wherein the weight ratio of (b) to (c) in the composition is at about 1:1; and
    wherein the composition is free of sulfate-containing anionic surfactants.

2. A process for the care of hair and/or scalp, comprising contacting a keratinous substrate with the composition of claim 1.

3. The composition according to claim 1, wherein (b) is present in the composition in a total amount ranging from about 0.01 to about 2% by weight relative to the total weight of the composition.

4. The composition according to claim 1, wherein (c) is present in the composition in a total amount ranging from about 0.05 to about 5% by weight relative to the total weight of the composition.

5. The composition according to claim 1, wherein (d) comprises cocamidopropyl betaine and coco-betaine which are present in the composition in a weight ratio of about 2:1.

6. The composition according to claim 1, wherein (e) is chosen from cationic polymers, ampholytic polymers, natural oils, synthetic oils, fatty esters, and mixtures thereof.

7. The composition according to claim 1, wherein (e) is chosen from polyquaternium-10, polyquaternium-7, polyquaternium-39, polyquaternium-53, and mixtures thereof.

8. The composition according to claim 1, wherein the aqueous medium includes water or mixtures of water and at least one cosmetically acceptable solvent chosen from C1-C4 lower alcohols, polyols, and polyol monoethers.

9. The composition according to claim 1, wherein the composition is a cleansing composition.

* * * * *